United States Patent [19]

Chet et al.

[11] Patent Number: 4,748,021

[45] Date of Patent: May 31, 1988

[54] ANTIFUNGAL COMPOSITIONS CONTAINING TRICHODERMA ACTIVE AGAINST FUSARIUM

[75] Inventors: Ilan Chet; Alex Sivan, both of Ness Ziona, Israel

[73] Assignee: Yissum Research and Development Company of the Hebrew University of Jerusalem, Jerusalem, Israel

[21] Appl. No.: 634,883

[22] Filed: Jul. 27, 1984

[30] Foreign Application Priority Data

Jul. 28, 1983 [IL] Israel .................................... 69368

[51] Int. Cl.$^4$ ..................... C12N 5/00; A61K 37/00
[52] U.S. Cl. .................................. 424/93; 435/242; 435/254
[58] Field of Search ................. 424/93; 435/254, 242, 435/945, 255; 47/58

[56] References Cited

FOREIGN PATENT DOCUMENTS 0133878  4/1984  European Pat. Off. ............. 435/70
0124388  11/1984  European Pat. Off. ............. 435/70

OTHER PUBLICATIONS

Bell et al., *Phytopathology*, vol. 72(4) 1982, pp. 374–382, "The Antagonism of Trichoderma Species Against Six Fungal Pathogens".

Elad et al., *Can J. Microbiol*, vol. 28, 1982, pp. 719–725, "Degradation of Plant Pathogenic Fungi By *Trichoderma harzianum*".

Csinos et al., *Chem Abst*, vol. 100, No. 1341644, 1984, "Evaluation of Trichoderma Spp. Fungicides and Chemical Combination for Control of Southern Stem Rot on Peanuts".

Marois et al., *Phytopathology*, 1981, vol. 77, pp. 1257–1260.

*Primary Examiner*—Thomas G. Wiseman
*Assistant Examiner*—Robin Lyn Teskin
*Attorney, Agent, or Firm*—John P. White

[57] ABSTRACT

A biological control agent comprising the antifungal agent *Trichoderma harzianum* T-35 (ATCC No. 20691), which is characterized by antifungal activity against fungi of the genus Fusarium. This strain is useful for protecting most crops affected by the fungus Fusarium spp. and is more active than other previously disclosed strains. Biocontrol compositions containing *T. harzianum* T-35 (ATCC No. 20691) provide antifungal protection to a broad spectrum of plants, including wheat, cotton, melons and tomatoes.

16 Claims, No Drawings

ANTIFUNGAL COMPOSITIONS CONTAINING TRICHODERMA ACTIVE AGAINST FUSARIUM

FIELD OF THE INVENTION

The present invention relates to antifungal compositions, particularly to biological control compositions containing *Trichoderma harzianum* and to methods of protecting plants from soil-borne pathogenic fungi with such compositions.

BACKGROUND OF THE INVENTION

Soil-borne pathogenic fungi causes damping off, root-rot, crown-rot and neck-rot in a wide variety of seedling crops. Among these pathogenic fungi are fungi of the genera Rhizoctonia, Pythium, Sclerotium, Phytophotora and Fusarium. These fungi are capable of attacking and causing extensive damage to many common and commercially important crops, such as wheat, beans, tomatoes, cotton, peanuts, potatoes, melons, lettuce, ornamental flowers and others. Fusarium spp. in particular has an extraordinarily wide host range and is capable of attacking many commonly grown and commercially important crops.

*F. roseum* "Culmorum", for example, is a cosmopolitan pathogen occurring on an extremely wide range of host plants, including wheat. *F. roseum* "Culmorum" is of economic significance, since it is a causal agent of cortical rots and pre- and post emergence blight.

*F. oxysporum* spp. are also commercially significant pathogens. *F. oxysporum* f. sp. *radicis-lycopersici* causes crown rot in tomatoes. Unlike other strains of *F. oxysporum*, *F. oxysporum* f. sp. *radicis-lycopersici* is a causal agent of stem rot. Other destructive *F. oxysporium* spp. are f. sp. *vasinfectum* which attacks crops including cotton, and f.sp. *melonis* which attacks melon crops. These pathogens are world-wide agricultural problems.

Chemical fungicides have been widely used to control these soil-borne pathogens. The use of such chemicals is expensive and may result in ecological damage and in the increased incidence of occupational diseases. One particular problem in controlling Fusarium spp. infestation in crops is the fact that most chemical fungicides are not sufficiently effective. Only systemic fungicides result in some positive result, and even those are only partially effective. The method most commonly used today is soil fumigation with methyl bromide and chloropicrin, at high application rates prior to planting. A promising alternative to such chemical control is the biological control of soil-borne plant pathogens by naturally-occurring microorganisms. These biological control agents may be used alone or in conjunction with lesser amounts of chemical fungicides.

The use of antagonistic microorganisms in controlling plant pathogenic fungi has been the subject of extensive research. A large part of this research has been concerned with myco parasitism, the parasitism by one fungus of another. One of the most frequently studied mycoparasites in relation to biological control is the genus Trichoderma. (Y. Elad et al., 1982, Can. J. Microbiol. 28: 719-725, I. Chet and R. Baker, 1981, Phytopathology 71: 286-290; M. N. Schroth and J. G. Hancock, 1981, Ann. Rev. Microbiology 35: 459-463; Y. Elad et al., 1981, Plant Disease 65: 675-677; Y. Elad, et al., 1980, Phytopathology 70: 119-121; I. Chet et al., 1979, in B. Scippers and W. Gams, eds, "Soil Borne Plant Pathogens", Academic Press, NY, NY; Y. Hadar et al., 1979, Phytopathology 69: 64-68; C. Dennis and J. Webster, 1971, Trans. Br. mycol. Soc. 57(3), 363-369).

Species or strains of Trichoderma may be differentially antagonistic to different species of fungi. (H. D. Wells et al., 1972, Phytopathology 62: 442-447). Such differences in antagonism have been found both within and between species of Trichoderma (D. K. Bell et al., 1982, Phytopathology 72: 379-382).

It was thus found that the species *T. harzianum* and *T. hamatum* showed high fungicidal activity, especially against *Sclerotium rolfsii* and *Rhizoctonia solani*. *T. hamatum* was also found to be effective against Phythium spp.

In addition to such differences in antagonism, it has been determined that the environment in which the interaction occurs also affects the degree of biological control. Antagonism in culture is often not reproducible in the complex environment present in the soil under greenhouse or field conditions. (M. N. Schroth and J. G. Hancock, 1981, Ann. Rev. Microbiol. 35: 453-76). As a result, tests made under non-soil culture conditions are not truly indicative of the potential for use of the Trichoderma isolate as a biological control agent.

Due to the significant differences in antagonism of Trichoderma isolates to various pathogens under different environmental conditions, researchers have concentrated their efforts on searching for Trichoderma antagonists against specific disease causing plant pathogenic fungi.

One strain of *Trichoderma harzianum*, *T. harzianum* Rifai T-315 (ATCC No. 20671) has been found to be effective in combating several pathogenic fungi, and exhibits some antagonistic activity against Fusarium spp. (co-owned and copending U.S. Ser. No. 588,950, filed Mar. 31, 1984). As in the case of chemical fungicides, however, *T. harzianum* T-315 (ATCC No. 20671) is only partially effective in protecting crops from Fusarium spp. Thus the need for specific and highly effective agents which are antagonistic to Fusarium spp. has heretofore remained unmet.

SUMMARY OF THE INVENTION

This invention concerns the strain *Trichoderma harzianum* T-35 (ATCC No. 20691) which is useful as a biological control agent, having significant antifungal activity against pathogenic fungi of the genus Fusarium or mutants thereof. *T. harzianum* T-35 (ATCC No. 20691) is especially useful in the control of *F. roseum* "Culmorum" and *F. oxysporum*, specifically *F. oxysporum* f. sp. *vasinfectum*, f. sp. *radicis-lycopersici* and f. sp. *melonis*. One preferred embodiment of the invention is a biologically pure culture of *T. harzianum* T-35 (ATCC No. 20691).

*Trichoderma harzianum* T-35 (ATCC No. 20691) may be mixed with a suitable agriculturally acceptable carrier to produce an antifungal biocontrol composition useful in controlling diseases caused by soil-borne plant pathogenic fungi. This biocontrol composition may also contain a food base for the antifungal agent or the carrier itself may also serve as the food base.

The invention also concerns methods of using this antifungal biocontrol composition. Effective amounts of the biocontrol composition are applied to or incorporated in soil in which plant seedlings are grown. Potted seedlings may also be protected from attack by soil-borne pathogenic fungi by potting them in soil containing an effective amount of the biocontrol composition.

In a specific embodiment of the invention the soil is sterilized, e.g., with methyl bromide, before the application of a biocontrol composition containing the T-35 strain.

In other embodiments of the invention the biocontrol composition also contains a suitable agriculturally acceptable adhesive. This biocontrol composition is used to coat fruits and plant seeds in order to protect them from diseases caused by soil-borne pathogenic fungi.

DETAILED DESCRIPTION OF THE INVENTION

In one aspect of this invention, a strain of *Trichoderma harzianum* was found to have antifungal activity against pathogenic fungi of the genus Fusarium or mutants thereof. This strain was isolated from a soil naturally infested with Fusarium spp. and was given the number T-35. It has been cultured in a biologically pure form. The preferred strain *Trichoderma harzianum* T-35, is deposited with the American Type Culture Collection, Rockville, Md. 20852, pursuant to the provisions of the Budapest Treaty on the International Recognition of the Deposit of Microorganisms for the Purposes of Patent Procedure under accession number ATCC 20691.

This isolate exhibits greater antifungal activity against Fusarium spp. than any other Trichoderma species isolated to date, including the *T. harzianum* reported by J. J. Marois et al., Phytopathology, 1981, Vol. 71, pages 1257–1260.

While *T. harzianum* T-35 (ATCC No. 20691) did not attack *F. oxysporum* f. sp. *vasinfectum* or f. sp. *melonis* under laboratory conditions, it was surprisingly found to be quite effective against these fungi as well as against *F. oxysporum* f. sp. *radicis-lycopersici* in greenhouse tests and preliminary field trials. The T-35 strain is also effective in controlling *F. roseum* "Culmorum". Indeed, compositions containing the T-35 strain are effective in protecting most crops affected by the fungus Fusarium spp., including wheat, tomatoes, cotton and melons.

A particular feature of the present invention is that *T. harzianum* T-35 (ATCC No. 20691) controls diseases caused by Fusarium spp. throughout a 20° C. to 35° C. temperature range although a temperature of up to 32° C. is preferred. This characteristic makes this embodiment a versatile biocontrol agent suitable for application in semi-arid as well as in temperate agricultural zones.

The *T. harzianum* T-35 strain can be propagated by any of the known procedures from the pure culture. One such method is described by Elad et al. (1981) Plant Diseases, 65: (8), 675–677.

There are a variety of possible methods of applying the present invention. One method is the application of conidia or chlamydospores or mixtures of the two, from *T. harzianum* T-35 (ATCC No. 20691) directly to the soil. The active antagonistic structures of Trichoderma spp. are its spores, including conidia spores, which germinate upon inoculation into soil and the chlamydospores, the fungal long-term survivable resting structures. Direct application of the antifungal agent, however, seems to be less effective than the application of a biocontrol composition which contains an agriculturally acceptable carrier. The biocontrol compositions may be applied directly to the soil in which the plant is growing, or the seedling itself may be potted in soil containing an effective amount of the biocontrol composition.

These biocontrol compositions may be in a solid or liquid form and may include other adjuvants such as emulsifiers, suspending agents, sticking agents etc. The solid compositions may be in the form of dusts, granules, or wettable powders, whereas the liquid compositions may be in the form of aqueous or non-aqueous media, in solution, suspension, dispersion or concentrate form.

The quantity of spores, conidia or chlamydospores, of the antifungal agent(s) in the composition should be at least $10^5$ and preferably above $10^7$ spores per gram of composition. Propagation of these spores depends upon growth conditions within the composition or in the soil to which it is applied. Such factors as the storage time of the composition may have an effect on the growth conditions of the composition and therefore it is preferred to prepare compositions which contain a suitable food base.

In certain embodiments of the invention the carrier may constitute wholly or in part a food base for the antifungal agent. Such food bases are known to those of ordinary skill in the art and may constitute agricultural waste products. Some suitable food bases include wheat bran, peat, milled corn cobs, ground wheat straw, and ground cotton straw. A preferred food base is a 1:1 mixture of wheat bran and peat. These food bases are usually sterilized and moistened.

The food base and carrier provide the antifungal agent with sufficient nutrients and a favorable microenvironment facilitating its establishment and long term survival in the soil.

Embodiments of the biocontrol composition may also contain another pesticide. The pesticide may be another biocontrol agent such as a mycoparasite or antifungal agent of a different species of Trichoderma. Thus the biocontrol composition may contain a mixture of *T. harzianum* T-35 (ATCC No. 20691) and other biocompatible antifungal agents, e.g., *T. harzianum* T-315 (ATCC No. 20671) to afford broad spectrum antifungal protection.

For application in the fields, ten to five hundred grams and preferably fifty to one hundred grams (dry weight), of the biocontrol composition are applied to each square meter of soil. The biocontrol composition is spread in the seeding rows and then incorporated into the soil. In the greenhouse, the biocontrol composition is applied at the rate of one to ten grams (dry weight) per kilogram of soil and preferably at the rate of five grams per kilogram of soil.

In a specific embodiment of the invention, the biocontrol composition also contains a suitable agriculturally acceptable adhesive, e.g., Pelgel ® (Nitragin, Wisc. USA) or NU-FILM-17 (Miller Chemicals, Penn. USA). This biocontrol composition containing the adhesive can be applied to seeds as a seed coating before planting, and also to fruits in order to protect them from diseases caused by soil-borne pathogens.

The range of host plants that are subject to attack by Fusarium spp. is very broad. This invention is effective in controlling diseases caused by this soil-borne pathogen over this wide range, and is effective in protecting such plants as wheat, melons, tomatoes, cotton and other seedlings.

EXAMPLES

Example 1

A strain of *Trichoderma harzianum* was isolated from a soil naturally infested with Fusarium species as follows:

1 g sample of the soil was suspended in 100 g water and shaken at 400 rpm. Portions of the liquid were diluted with a 0.01% bacto-agar solution three times and 0.1 ml of the serial dilutions were grown on selective media agar plates (Elad et al., Phytoparasitica, 1981, Vol. 9, pages 59–67). The resultant pure strain was named T-35. This isolate was grown for fourteen days at 30° C. on a 1:1 wheat bran:peat, tap water mixture (40% water) which was autoclaved for one hour at 121° C. on three successive days.

Example 2

*Trichoderma harzianum* T-35 (ATCC No. 20691) was grown on agricultural wastes as food bases and was incubated at the temperature of 30° C. for a week and then tested for growth rate. Growth vigor and survivability were quite satisfactory.

Wheat bran, peat or a mixture of the two appear to be the food bases best utilized by the Trichoderma. Other food bases, however, are also quite acceptable.

Example 3

*Trichoderma harzianum* T-35 (ATCC No. 20691) was incorporated into a composition comprising wheat-bran:peat (1:1) (v/v) (40% (w/w) moistened), hereinafter referred to as T-35 composition. The composition was applied to soils at 5 g composition/kg soil in the greenhouse.

Example 4

Melon seed were coated with *Trichoderma harzianum* T-35 (ATCC No. 20691) conidia, using NU-FILM 17 adhesive (Miller Chemicals, Penn. USA) as an adhesive matrix. The coated seeds were planted in greenhouses in soil from Rehovot artificially infested by the addition thereto of $3 \times 10^9$ microconidia Fusarium spp. per kilogram soil. The treated seeds effectively prevented infestation of the crop with *Fusarium oxysporum* f. sp. *melonis* compared to an untreated control, as shown in Table 1.

Example 5

Melon seeds coated as in Example 4 were planted in greenhouses in heavy soil taken from Kafar Manda (Israel) which was naturally infested with Fusarium spp. The effectiveness of T-35 against *Fusarium oxysporum* f. sp. *melonis* after 14 and 24 days is shown in Table 2.

TABLE 2

| | 14 days | | 24 days | |
|---|---|---|---|---|
| Treatment | diseased plants % | disease reduction % | diseased plants % | disease reduction % |
| Control | 9.3 | — | 23.8 | — |
| T-35 coated seeds | 0 | 100 | 7.8 | 67.2 |

Example 6

Soil from Rehovot was sterilized by autoclaving for one hour. The soil was infested artificially with $3 \times 10^9$ microconidia *Fusarium oxysporum* f. sp. *vasinfectum* per kilogram soil. *T. harzianum* T-35 was incorporated into the soil as a composition comprising wheat bran:peat (1:1) v/v (5 gram composition per kg. soil). The experiment was carried out with cotton in greenhouses. The results are tabulated in Table 3.

TABLE 3

Effect of *T. harzianum* T-35 (ATCC No. 20691) compositions comprising wheat bran: peat on Fusarium spp. in cotton planted in artifically infested soil (30 days after planting)

| Treatment | Diseased plants % | Disease reduction % |
|---|---|---|
| Control | 52.7 | — |
| Compositions containing T-35 | 5.6 | 89.4 |

Example 7

Natural soil of Rehovot was infested with Fusarium spp. as in Example 6 and a composition comprising *T. harzianum* in wheat bran:peat 1:1 (v/v) was incorporated into the soil (5 g. per kg soil). Cotton was planted in this soil in greenhouses, and the plants were inspected after 17, 20 and 26 days for disease. The results are shown in Table 4.

TABLE 4

Effect of Composition of *T. harzianum* T-35 v(ATCC No. 20691) in Wheat Bran:Peat on Fusarium spp. in Cotton Plants in Natural Infested Soil.

| | 17 days | | 20 days | | 26 days | |
|---|---|---|---|---|---|---|
| Treatment | diseased plants % | disease reduction % | diseased plants % | disease reduction % | diseased plants % | disease reduction % |
| Control | 36 | — | 50 | — | 75 | — |
| Composition containing T-35 | 0 | 100 | 5.3 | 89.4 | 10.5 | 86.0 |

TABLE 1

Effect of *T. harzianum* T-35 (ATCC No. 20691) Seed Coating on the Control of Fusarium spp. in Melon Plants. (after 24 days)

| Treatment | Diseased Plants % | Disease reduction % |
|---|---|---|
| Control | 76.4 | — |
| T-35 coated seeds | 15.8 | 79.3 |

Example 8

A *T. harzianum* T-35 (ATCC No. 20691) composition comprising wheat bran and peat 1:1 (v/v) was incorporated into soil containing Fusarium spp. as in Example 6. Cotton seeds were planted and after 30 days the plants were inspected for infestation. Then the plants were uprooted and the soil was mixed and replanted with more cotton seeds. The second crop was again evaluated for infestation after 30 days. The results are shown in Table 5.

TABLE 5
Effect of T-35 Composition on Fusarium spp. in Cotton upon Repeated Planting.

| Treatment | 1st planting | | 2nd planting | |
|---|---|---|---|---|
| | diseased plants % | disease reduction % | diseased plants % | disease reduction % |
| Control | 80.0 | — | 90.9 | — |
| T-35 composition | 31.7 | 60.4 | 29.3 | 67.8 |

Example 9

Comparative tests were conducted to show the effect of *T. harzianum* T-35 (ATCC No. 20691) against Fusarium spp. compared with the effect of *T. harzianum* T-315 (ATCC No. 20671). The latter is very effective against the pathogen *P. aphanidermatum* and other fungi as disclosed in co-owned and copending U.S. Ser. No. 588,950, filed Mar. 13, 1984.

Cotton was planted in soil infested with Fusarium spp. and treated with the respective Trichoderma compositions (wheat bran:peat 1:1 v/v) as in Example 6. After 30 days the plants were inspected. The results are shown in Table 6.

TABLE 6
Comparative Effect of *T. harzianum* T-35 (ATCC No. 20691) and *T. harzianum* T-315 on Fusarium spp. in Cotton Plants (30 days after planting).

| Treatment | diseased plants % | disease reduction % |
|---|---|---|
| Control | 41.3 | — |
| T-35 | 1.9 | 95.4 |
| T-315 | 14.8 | 64.2 |

This experiment demonstrates that although *T. harzianum* T-315 (ATCC No. 20671) partially controls Fusarium spp., the *T. harzianum* T-35 (ATCC No. 20691) is quite superior in this respect.

Example 10

Comparative tests were conducted under greenhouse conditions to show the effect of various methods of application of *T. harzianum* T-35 (ATCC No. 20691) against *Fusarium roseum* "Culmorum" in wheat, *Triticum aestivum* L. cv. Miriam. Wheat seeds were soaked in a macroconidial suspension of *F. roseum* "Culmorum" ($5.5 \times 10^6$ macroconidia/ml; 2.4 ml/g seeds) and immediately dried by warm ventilation. Alternatively, the soil was inoculated with $5.5 \times 10^6$ macroconidia/kg soil. The various methods used to apply the *T. harzianum* T-35 were as follows: inoculation of the soil with a conidial suspension of the T-35 strain ($5 \times 10^9$ conidia/kg soil) or with a T-35 wheat bran/peat composition (5 g/kg soil), or coating the wheat seeds with the Trichoderma sp. T-35. Conidia for the seed coating were collected from *T. harzianum* T-35 cultures grown in erlenmeyer flasks, each containing 200 ml of solidified potato dextrose agar (PDA, Difco Laboratories). The conidial suspension, adjusted to $5 \times 10^9$ conidia/ml, was supplemented with 0.15% (v/v) of NU-FILM-17 adhesive (Miller Chemicals, Penn. USA.). Two ml of the resultant suspension were used to coat 20 g of seeds. The incidence of disease was assessed 30 days after planting. The results are shown in Table 7.

TABLE 7
Effect of Method of Application of *T. harzianum* T-35 (ATCC No. 20691) on Incidence of Disease in *Triticum aestivum* L. cv. Miriam Caused by *F. roseum* "Culmorum"

| Inoculation with *F. roseum* "Culmorum" | T-35 Application | Disease Incidence (%)[1] |
|---|---|---|
| seed[2] | —[4] | 44.4B |
| seed[2] | seed coating | 13.3C |
| soil[2] | —[4] | 51.8B |
| soil[2] | seed coating | 22.2C |
| soil[2] | conidial suspension | 16.6C |
| soil[2] | wheat bran/peat | 13.0C |
| soil[3] | —[4] | 76.6A |
| soil[3] | wheat bran/peat | 15.4C |

[1] Numbers followed by a common letter are not significantly different according to Duncan's multiple range test (P = 0.05).
[2] Soil previously untreated.
[3] Soil previously autoclaved.
[4] Control (no T-35).

Example 11

Tomato seeds, cv. Ayalon, were coated with *T. harzianum* T-35 (ATCC No. 20691) as in Example 10. The coated seeds were grown in sandy loam soil from the Rehovot, Israel area which was inoculated with $2 \times 10^8$ microconidia *F. oxysporum* f. sp. *radicis-lycopersici* per kg soil. The experiment was conducted in plastic pots, each containing 4 kg of soil, under greenhouse conditions. The tomato plants grown from treated seeds exhibited a reduced incidence of crown rot, as measured by the percentage of plants wilted. The results are shown in Table 8.

TABLE 8
Effect of *T. harzianum* T-35 (ATCC No. 20691) Seed Coating on the Control of Crown Rot in Tomatoes Caused by *F. oxysporum* f. sp. radicis-lycopersici

| Days from Planting | % of plants wilted | | | | |
|---|---|---|---|---|---|
| | 28 | 41 | 65 | 68 | 74 |
| Control | 10 | 20 | 31.4 | 47.1 | 85.7 |
| T-35 coating | 2 | 11.25 | 12.8 | 17.1 | 40 |

Similar results may be obtained by coating the seeds as in Example 4. Alternatively, the seeds in this and other examples may be coated by the following procedure: suspend Trichoderma spores in distilled water at a concentration of $10^8$ spores/ml; add COLFIX (40% vinyl resin) (Jewnin-Joffee Industry Ltd., Tel Aviv, Israel) to create a 0.1% solution; spread an aliquot of 0.9–1.2 ml of the mixture evenly over 100 seeds and immediately dry in a stream of warm air.

What is claimed is:

1. A biologically pure, stable culture of an *Trichoderma harzianum* T-35 (ATCC No. 20691) useful as a biological control agent and having anti-fungal activity against pathogenic fungi of the genus Fusarium or mutants thereof.

2. A biocontrol composition characterized by antifungal activity against pathogenic fungi of the genus Fusarium comprising an effective amount of the culture of claim 1 and a suitable agriculturally acceptable carrier.

3. A biocontrol composition in accordance with claim 2, wherein the *Trichoderma harzianum* T-35 (ATCC No. 20691) present in the culture is in the form of conidia or chlamydospores or mixtures thereof.

4. A biocontrol composition in accordance with claim 3, wherein the concentration of *Trichoderma har-*

*zianum* T-35 is at least $10^5$ spores per gram of composition.

5. A biocontrol composition in accordance with claim 2, wherein the carrier include a food base for *Trichoderma harzainum* T-35.

6. A biocontrol composition in accordance with claim 2, which also comprises a suitable agriculturally acceptable adhesive.

7. A biocontrol composition in accordance with claim 2 which also comprises another different strain of *Trichoderma harzianum* in the culture.

8. A biocontrol composition in accordance with claim 3, wherein the Fusarium spp. is *F. oxysporum* f. sp. *radicis-lycopersici,* f. sp. *melonis,* f. sp. *vasinfectum* or *F. roseum* Culmorum.

9. A method of protecting plants from diseases caused by Fusarium spp. pathogenic fungi which comprises incorporating in or applying to the soil in which seedlings are grown an effective amount of agent of a biologically pure, stable culture of the strain *Trichoderma harzianum* T-35 (ATCC No. 20691) useful as a biological control agent and having antifungal activity against pathogenic fungi of the genus Fusarium or mutants thereof.

10. A method of protecting plants from disease caused by Fusarium spp. pathogenic fungi which comprises incorporating in or applying to the soil in which the plants are grown an effective amount of a biocontrol composition characterized by antifungal activity against pathogenic fungi of the genus Fusarium comprising an effective amount of the culture of claim 1 and a suitable agriculturally acceptable carrier.

11. A method in accordance with claim 10, wherein the soil is first sterilized.

12. A method in accordance with claim 11, wherein the soil is sterilized by fumigation with methyl bromide.

13. A method of protecting fruits from diseases caused by Fusarium spp. pathogenic fungi comprising applying to the fruits an effective amount of a biocontrol composition characterized by antifungal activity against pathogenic fungi of the genus Fusarium comprising an effective amount of the culture of claim 1 and a suitable agriculturally acceptable carrier.

14. A method of claim 13, wherein the biocontrol composition also comprises a suitable agriculturally acceptable adhesive.

15. A method of protecting plant seeds from diseases caused by Fusarium spp. pathogenic fungi comprising applying to plant seeds an effective amount of a biocontrol composition characterized by antifungal activity against pathogenic fungi of the genus Fusarium comprising an effective amount of the culture of claim 1 and a suitable agriculturally acceptable carrier.

16. A method of claim 15, wherein the biocontrol composition also comprises a suitable agriculturally acceptable adhesive.

* * * * *